US008086317B2

(12) United States Patent
Finch et al.

(10) Patent No.: US 8,086,317 B2
(45) Date of Patent: Dec. 27, 2011

(54) SYSTEM AND METHOD FOR ELECTRICAL STIMULATION OF THE INTERVERTEBRAL DISC

(75) Inventors: Philip M. Finch, Parkerville (AU); Scott F. Drees, McKinney, TX (US); John Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 12/917,827

(22) Filed: Nov. 2, 2010

(65) Prior Publication Data

US 2011/0046695 A1    Feb. 24, 2011

Related U.S. Application Data

(63) Continuation of application No. 11/426,466, filed on Jun. 26, 2006, now Pat. No. 7,831,306, which is a continuation of application No. 10/318,741, filed on Dec. 13, 2002, now Pat. No. 7,069,083.

(51) Int. Cl.
*A61N 1/34* (2006.01)
(52) U.S. Cl. ............... 607/46; 607/43; 607/117
(58) Field of Classification Search .......... 607/43, 607/46, 117
See application file for complete search history.

(56) References Cited

U.S. PATENT DOCUMENTS

| 4,044,774 | A | 8/1977 | Corbin et al. |
|---|---|---|---|
| 4,549,556 | A | 10/1985 | Tarjan et al. |
| 4,800,898 | A | 1/1989 | Hess et al. |
| 5,121,754 | A | 6/1992 | Mullett |
| 5,255,691 | A | 10/1993 | Otten |
| 5,342,409 | A | 8/1994 | Mullett |
| 5,417,719 | A | 5/1995 | Hull et al. |
| 5,433,739 | A | 7/1995 | Sluijter et al. |
| 5,733,322 | A | 3/1998 | Starkebaum |
| 5,824,021 | A | 10/1998 | Rise |
| 5,938,690 | A | 8/1999 | Law et al. |
| 5,980,504 | A | 11/1999 | Sharkey et al. |
| 6,002,964 | A | 12/1999 | Feler et al. |
| 6,007,570 | A | 12/1999 | Sharkey et al. |
| 6,014,588 | A | 1/2000 | Fitz |
| 6,073,051 | A | 6/2000 | Sharkey et al. |
| 6,095,149 | A | 8/2000 | Sharkey et al. |
| 6,104,957 | A | 8/2000 | Alo et al. |
| 6,122,549 | A | 9/2000 | Sharkey et al. |

(Continued)

OTHER PUBLICATIONS

Indahl A; Kaigle AM; Reikeras O; Holm SH; Spine clinic, Ostfold Central Hospital, Fredrikstad, Norway, Spine (US), Dec. 15, 1997, 22 (24), p. 2834-40.

(Continued)

*Primary Examiner* — Michael Kahelin
(74) *Attorney, Agent, or Firm* — Christopher S. L. Crawford; Craig Hoersten; Melissa Acosta

(57) ABSTRACT

In one embodiment, a method electrically stimulates an area in a spinal disc. The method comprises: implanting at least one steerable lead at a placement site for stimulating a spinal disc such that the lead is disposed exterior and immediately adjacent to and circumferentially along an annulus of the spinal disc, the at least one lead including a plurality of electrodes distributed along a majority of a circumference of the annulus; connecting the lead to a signal generator; and generating electrical stimulation pulses using the generator to stimulate targeted portions of the spinal disc, wherein the stimulation of the targeted portion of the spinal disc sufficiently stimulates nerve tissue within the spinal disc to prevent communication of pain signals originating in the spinal disc without damaging tissue of the spinal disc.

7 Claims, 7 Drawing Sheets

U.S. PATENT DOCUMENTS

| | | | |
|---|---|---|---|
| 6,146,380 | A | 11/2000 | Racz et al. |
| 6,161,047 | A | 12/2000 | King et al. |
| 6,258,086 | B1 | 7/2001 | Ashley et al. |
| 6,314,325 | B1 | 11/2001 | Fitz |
| 6,360,750 | B1 | 3/2002 | Gerber et al. |
| 6,408,214 | B1 | 6/2002 | Williams et al. |
| 6,558,390 | B2 | 5/2003 | Cragg |
| 6,689,132 | B2 | 2/2004 | Biscup |
| 6,736,815 | B2 | 5/2004 | Ginn |
| 7,069,083 | B2 | 6/2006 | Finch et al. |
| 2002/0151948 | A1 | 10/2002 | King et al. |
| 2003/0078633 | A1 | 4/2003 | Firlik et al. |

OTHER PUBLICATIONS

"Nerve Ingrowth into Diseased Intervertebral Disc in Chronic Back Pain," Lancet, vol. 350 Issue 9072, p. 178, Jul. 1997.

PCT International Search Report in International Application No. PCT/US 03/39434, dated May 3, 2004.

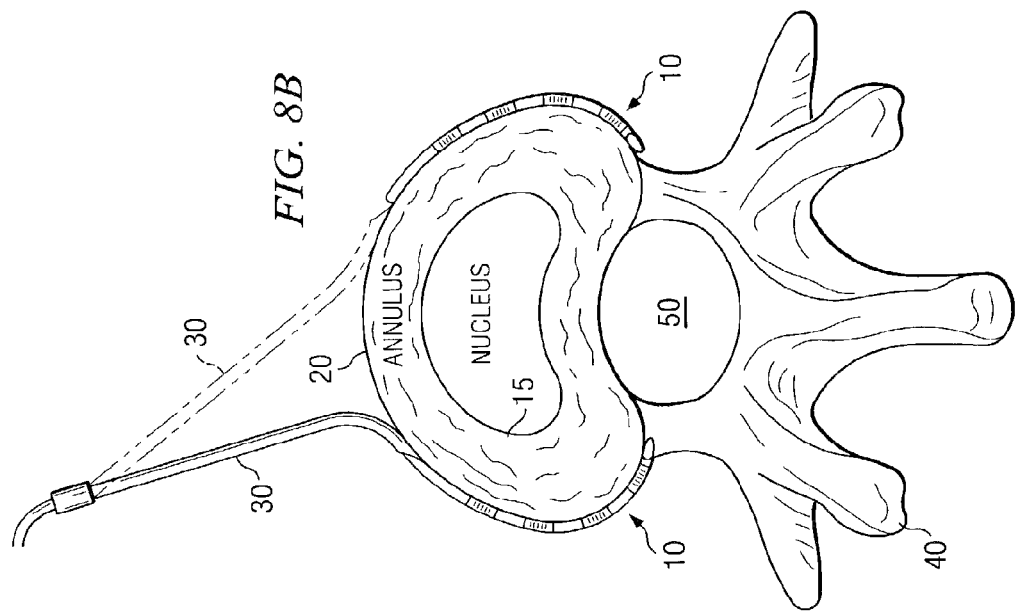
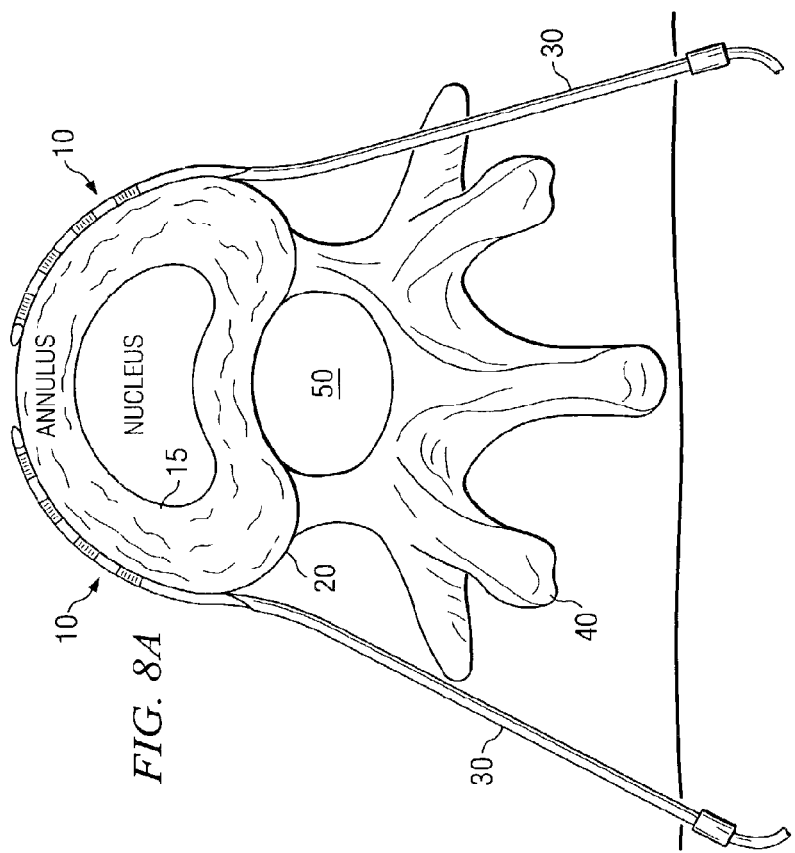

SYSTEM AND METHOD FOR ELECTRICAL STIMULATION OF THE INTERVERTEBRAL DISC

CROSS-REFERENCE TO RELATED APPLICATIONS

This application is a continuation of U.S. application Ser. No. 11/426,466, filed Jun. 26, 2006, now U.S. Pat. No. 7,831,306, which is a continuation of U.S. application Ser. No. 10/318,741, filed Dec. 13, 2002, now U.S. Pat. No. 7,069,083, the disclosures of which are incorporated herein by reference.

TECHNICAL FIELD

The present application relates generally to pain relief for spinal pain, and more generally to a system and method for electrical stimulation of the intervertebral disc to relieve pain.

BACKGROUND

The use of electrical stimulation of the spinal cord or associated nerve bundles for the reduction of bodily pain is well known in the art of pain relief. Leads containing electrodes are commonly used for such electrical stimulation and are implanted on or near a nerve bundle or the spinal cord. A pulse generator that supplies electrical pulses with predetermined characteristics is typically connected to the lead.

In a typical embodiment of the prior art, a stimulating lead incorporating multiple electrodes is constructed in a cylindrical, elongated and flexible lead configuration. The lead is then inserted into the spinal canal's epidural space and adjacent to the posterior aspect of the spinal cord. Alternatively, a lead may be inserted into the body next to or alongside the desired peripheral nerve.

A pulse generator transmits electrical pulses through two or more connecting wires within the lead to the electrodes, which by its proximity to the desired stimulation site, stimulates a certain area of the spinal cord or the peripheral nerve. In the case of spinal cord stimulation, the electrical pulse at the electrodes can negate the passage of pain sensation from peripheral areas such as a leg or arm, to the brain.

In the case of a lead inserted to lie alongside a peripheral nerve, stimulation of the nerve induces depolarization of the nerve and propagation of a nerve impulse towards the spinal cord. This also appears to negate unpleasant sensations conducted in the nerve. Various peripheral nerves have been stimulated by this latter technique including peripheral nerves to the limbs and to the cranium.

Multiple configurations of products and nerve stimulation currently exist. Papers by Holsheimer entitled "Effect of anode-cathode configuration on paresthesia coverage in spinal cord stimulation" and Hassenbusch, et. al. entitled "Long-term results of peripheral nerve stimulation for Reflex Sympathetic Dystrophy" describe various aspects of nerve stimulation and are incorporated by reference here in full.

Power to and control of such stimulating electrodes is derived from either fully implantable battery powered devices or generators, or alternatively, from radiofrequency systems, where the power is transmitted through the skin by closely applied transmitting coils. The Genesis® and Renew® systems, provided by Advanced Neuromodulation Systems, Inc. are two similar systems existing in the prior art that utilize this methodology. Such systems are further described in more detail in U.S. Pat. No. 4,793,353, which is incorporated by reference here in full.

Various configurations of leads have been designed and typically involve multiple electrodes of 2-3 mm in size, in multiples of 4 or 8. Such electrode arrays are inserted through an introducing needle into the epidural space, or in the case of a peripheral nerve are placed adjacent to the nerve either through a hollow needle or by open surgery. The power source and the electrode array are typically connected by a subcutaneous borrowed connector, which passes around the body to a suitable location such as the groin or lateral chest wall.

These products have been developed for treatment of chronic pain often where nerves have been injured or involved in surgery. Electrical stimulation provides a safe and minimally invasive means of controlling chronic pain without resorting to drugs.

The current treatment of discogenic (i.e., originating in the intervertebral disc) spinal pain is not satisfactory. Patients can be offered conservative management including physiotherapy treatment, medication and psychological techniques such as cognitive behavioral therapy. Presently, techniques exist of heating the annulus fibrosus using radiofrequency annuloplasty for painful annular tears causing discogenic low back pain.

This procedure is available for a relatively small group with only moderately degenerated discs. For a much larger group of patients with more advanced degeneration of the disc, often at multiple levels of the spine, presently, there is only surgery in the form of spinal fusion that can be offered.

Certain studies show that the results of spinal fusion are not ideal. For example, in the lumbar region only approximately 63% of patients improved, and approximately 30% experienced no improvement at all, or in some cases, worsening of the pain state.

Once a major operation such as a spinal fusion has been conducted, the anatomy of the spine is permanently changed. Secondary problems can also occur with altered mechanics of the spine, changes in nerve function and increased pressure on the discs at other spinal levels, which may need further surgery.

SUMMARY

A method for electrically stimulating an area in a spinal disc is presented. The method comprises implanting a lead with one or more electrodes in a placement site in a disc or just outside the outer confines of the disc, connecting the lead to a signal generator, and generating electrical stimulation pulses using the generator to stimulate targeted portions of the disc.

Additionally, a system for relieving pain associated with a spinal disc is presented that comprises a lead with one or more electrodes, an introducer for introducing the lead to a placement site in or just outside the confines of the disc, a removable stylet for guiding the lead to the placement site in the disc, and a generator connected to the lead for generating electrical pulses to the lead for stimulating the disc.

Finally, an insertable lead system is presented for relieving pain associated with a spinal disc that is inserted in a placement site inside or just outside the spinal disc, containing an introducer, a lead with one or more electrodes for stimulating an area in or just outside the spinal disc and an anchoring portion to anchor the lead in place either adjacent to or in the disc.

The foregoing has outlined some of the more pertinent objects and features of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the Preferred Embodiment.

BRIEF DESCRIPTION OF THE DRAWING

For a more complete understanding of some embodiments, reference is now made to the following descriptions taken in conjunction with the accompanying drawing, in which:

FIGS. 8A and 8B shows one embodiment of the present invention during implantation of the lead at the placement site adjacent to the disc;

DETAILED DESCRIPTION

Figure 1:
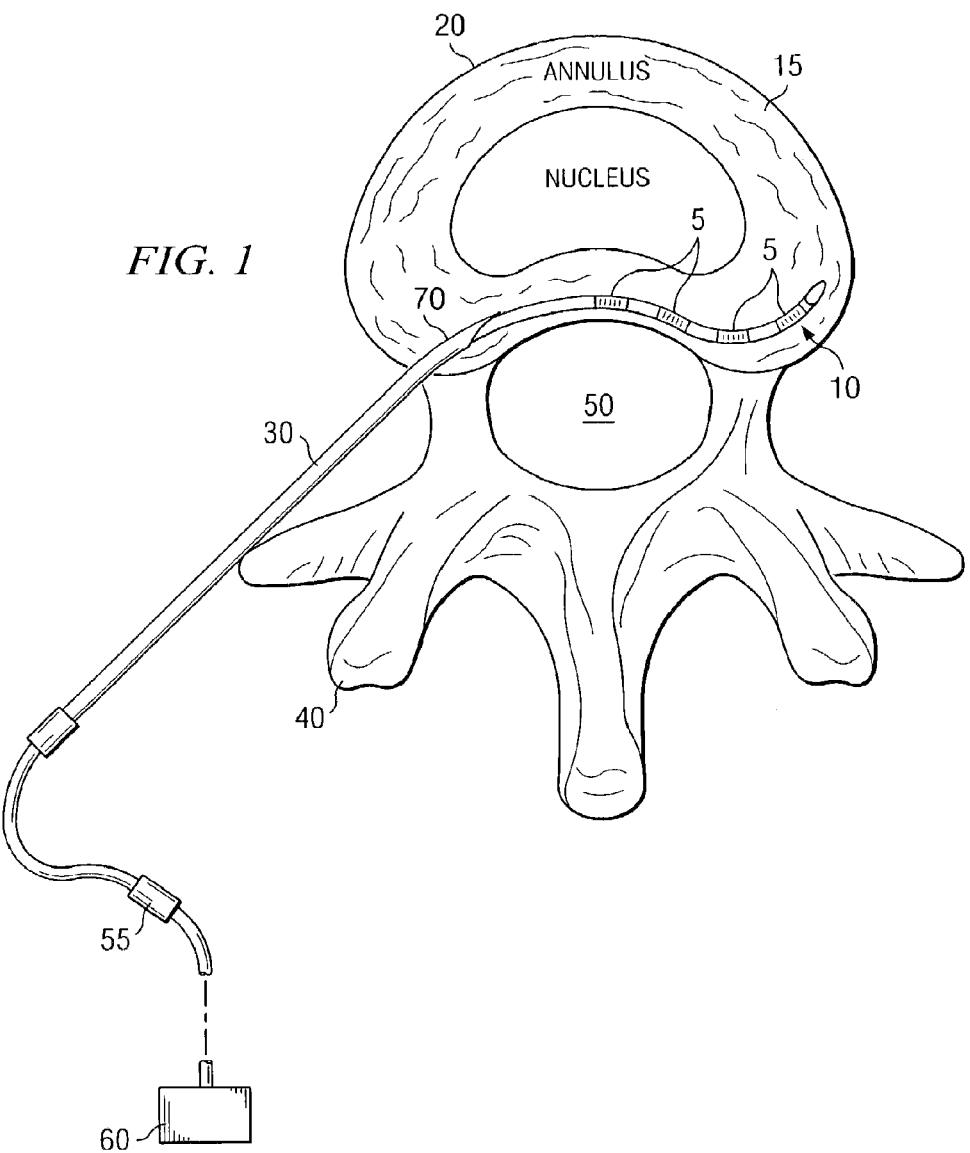
FIG. 1 shows a curved tip introducer inserted percutaneously into a lumbar intervertebral disc in accordance with one embodiment of the present.

The present invention treats the nerve-containing portion of the intervertebral disc for the indication of discogenic low back pain. The epidemiology of discogenic low back pain has been described by Deyo and Tsui-Wu in "Descriptive epidemiology of low-back pain and its related medical care in the United States," and Schwarzer, et. al., in "The sacroiliac joint in chronic low back pain" which are incorporated by reference here in full.

Pain can be derived from degeneration or tearing of the intervertebral disc, especially in its posterior or posterolateral portions. There is innervation of the intervertebral disc near the surface of the disc and also within its outer portion, known as the annulus fibrosus. Fissures or cracks within the discs, which appear with age, mechanical trauma or disc degeneration are believed to be associated with painful symptoms. It is thought that nerve fibers grow into such painful fissures or cracks and can even reach the outer part of the disc nucleus. Electrical stimulation of the disc at a specified placement site is configured to stimulate these nerve fibers and therefore negate unpleasant sensations originating in the disc. Such a placement site may be interior or adjacent to the disc in question.

Prior treatments for such discogenic low back pain relating to disc degeneration included a technique for heating portions of the annulus fibrosus with an intradiscal radiofrequency electrode. These treatments were performed for treatment of some forms of discogenic low back pain. This method typically heats or vaporizes a portion of the disc, possibly relieving interior disc pressure, thereby possibly relieving some associated disc pain. However, this procedure leads to a burning or scaring of the nerves associated with the disc, causing the pain relief to be temporary at best.

In the present invention, electrical stimulation of the nerve fibers associated with a disc is the primary methodology for pain relief. The patterns and spread of stimulation often invariably mimic the pattern of discogenic pain. Typically, for example in the lumbar region, this involves the spread of stimulation to involve the axial spine and the buttocks. If the voltage is increased, the spread can include the lower limbs. Previous attempts to stimulate the area of the axial spine have encountered difficulties. These difficulties, that despite complex multiple electrode systems, obtaining coverage of central discogenic pain can be difficult to cover, are well known in the art. Certain dual electrode systems have been developed by Advanced Neuromodulation Systems, Inc (ANS) to address these difficulties. These dual electrode systems are typically passed into the epidural space, to lie in the dorsolumbar area.

Stimulation can be obtained in the buttock and lower limbs by classical spinal cord stimulation with epidural leads placed in the epidural space. However, central discogenic low back pain can be difficult to cover. Typically, for analgesia to occur, the stimulated area must cover the area of the pain. The present invention uses direct stimulation of the intervertebral disc providing coverage of axial pain, which can provide greater certainty of coverage of these painful areas.

There are three main risks encountered from intradiscal manipulation, including nerve injury, migration of the lead away from the placement site to involve sensitive neural structures, and disc space infection. Certain studies have shown that the risk of disc space infection is considered to be approximately one in two thousand cases. This can be reduced by the injection of antibiotic into the disc at the time of implantation. The risk of nerve injury can be greatly reduced by very careful attention to surgical technique. The risk of migration of the lead can be minimized by the use of new materials for fixation of devices in or just adjacent to the disc space. Additionally, the risk can be minimized by placing the lead at a placement site that is adjacent to the disc in question, proximal to the injury site.

To additionally minimize the risks mentioned above, one embodiment of the present invention uses a configuration of a needle introducer to approach and enter the intervertebral disc. A lead is then inserted through the introducer. This configuration helps to adequately reach the posterior and posterolateral or any other desired portions of the intervertebral disc and places the lead at the correct placement site where the desired stimulation will occur. Thus, proper placement of the lead occurs and disc disruption is minimized using this embodiment.

Another embodiment of the present invention uses a configuration of the needle introducer to approach the desired location of the disc and place the lead, inserted through the introducer, at a placement site adjacent to the disc. This configuration helps to adequately reach the proper placement site where the desired stimulation will occur, without entering the intervertebral disc. The placement site corresponds to the location where lead placement optimizes disc pain relief.

For safety, it is desirable that the surgeon has quantitative information about the placement of the introducer and the stimulating lead as it is placed near the placement site in or just outside the disc. Additionally, risk of the lead kinking within the disc or straying outside the disc, which could result in damage to the probe or injury to the patient should be taken into account when considering the placement site. One embodiment of the present invention that minimizes the risk of kinking and allows for greater flexibility of choosing a placement site retains the lead in or adjacent to the intervertebral disc and prevents its migration.

In the present invention, prior to insertion of a permanent lead into or adjacent to the disc, a trial period is typically conducted for hours, days or even sometimes weeks. Trial insertion and stimulation can be conducted at the same time as the injection of radiographic contrast material into the disc. This provides the surgeon with information on fissures or cracks within the disc (i.e. discography) and the response of the nerves to electrical stimulation.

One embodiment of the present invention envisions that each patient who is diagnosed with discogenic low back pain, often by means of Magnetic Resonance Imaging and discography, will undergo a trial period of stimulation.

In this embodiment of the present invention, a trial lead will be inserted percutaneously at the placement site in the disc via an introducer and retained for a period while stimulation is conducted. The x-ray coordinates of the position and the electrical parameters of stimulation are noted during this period before complete removal of the trial stimulating device.

It is envisaged that such a trial stimulation lead will be similar to those currently utilized for periods of trial stimulation with ANS leads in the epidural space. The period of trial implantation could be short, lasting only a few hours or days, to minimize the chance of disc space infection or may be longer depending on the needs of the procedure and patient.

Figure 7:
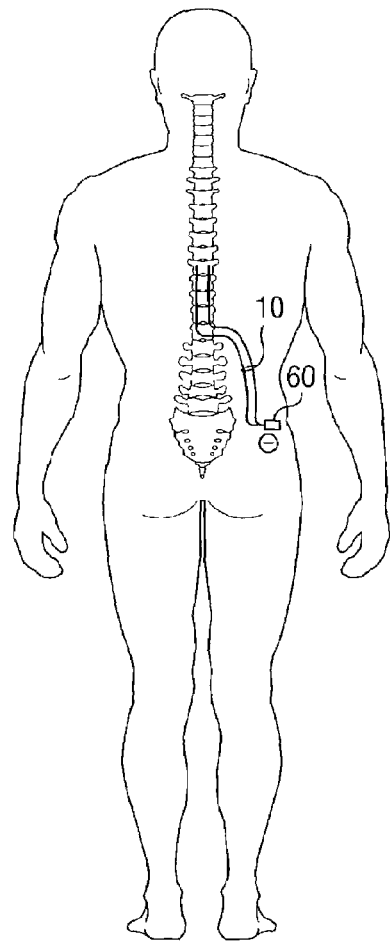
FIG. 7 shows one embodiment of the present invention inserted into a patient.

After due consideration of the results of the trial stimulation, a permanent lead is inserted at the placement site in or just outside the intervertebral disc for long term stimulation purposes. As shown in FIG. 7, lead 10, whether trial or permanent, will be connected to either a fully implanted, battery driven, stimulating device 60 that can last many years, or alternatively to a system for passage of external electrical energy through a coil or similar device often utilizing radiofrequency current. Stimulating device 60 is coupled to lead 10, which is place at the placement site. One embodiment of the present invention, stimulating device 60 is an implantable rechargeable device connected to the lead. Recharging of this device will be conducted by positioning of an external charging device adjacent to the implanted stimulator for a period of hours.

It is envisaged that the patient will require intermittent assessment with regard to patterns of stimulation. Different electrodes on the lead can be selected by suitable computer programming, such as that described in U.S. Pat. No. 5,938, 690, which is incorporated by reference here in full. Utilizing such a program allows an optimal stimulation pattern to be obtained at minimal voltages. This ensures a longer battery life for the implanted systems. Such programming will be conducted in a similar fashion to the current method of changing parameters for ANS stimulating systems.

One embodiment of the present invention uses a curved introducer to approach the placement site of the intervertebral disc via a percutaneous insertion point in the patient. The introducer is placed in or adjacent to the disc, depending on the actual location of the placement site, and a lead is passed through the introducer and pushed to the placement site in or adjacent to the intervertebral disc space. Appropriate steering of the lead will place the device at the placement site in close proximity to the tears and fissures so that the nerves innervating these fissures can be electrically stimulated.

The stimulating lead used in the present invention has a flexible configuration and is visible under image intensifier or CT X-ray monitoring. It is envisaged that in one embodiment, the lead passes through the intervertebral foramen, to exit the skin in the lumbar region. It is connected to an internal or external stimulating device so that variations of electrode configuration and electrical stimulation can be accomplished in a trial.

Various embodiments of a permanent lead are considered. In one embodiment a lead, which can be either monopolar (unipolar) or bipolar arrangement, can be inserted surgically, preferably by an endoscopic technique. This is typically performed in a similar fashion to endoscopic sympathectomy for lower limb ischaemia or endoscopic spinal fusion. This lead will have an unexpanded and an expanded position. The lead will be either inserted into the disc or placed adjacent to the disc so that it will expand into a position preventing migration onto adjacent sensitive neural structures.

The lead can have multiple electrical contacts or a single contact. It is then connected to a stimulating device, which is either fully implanted or powered by an external radiofrequency source, in the same fashion that current ANS devices are powered. It is envisaged that the lead will be constructed of biocompatible materials and designed such that it will resist migration and yet not prevent ultimate removal, if required. Such a anti-migration design includes an inflatable miniature balloon, surgical fixation device or a device consisting of material with elastic memory, such as silicon, polymers, polyurethane materials, or Nitinol or Nitinol coated with a biocompatible material.

Alternative techniques of placement of a permanent electrode or lead are envisaged, which are performed percutaneously. Such approaches involve the lateral portion of the disc to avoid placement of the lead adjacent to a nerve root or other sensitive neural structures. Additionally, the lead may lie just adjacent to the outer confines of the disc so that nerve fibers inside the annulus fibrosis are recruited.

It is envisaged that such placements would be performed under X-ray control and possibly in the same manner that permanent leads are placed in the epidural space. Connection of the stimulating leads in the disc would then be made to either a permanent implanted power source or a coil powered by an external device.

Referring to FIG. 1, one embodiment of the stimulating system in accordance with the present invention is generally illustrated. In this illustration, a trial lead 10 is passed across the posterior aspect of the annulus fibrosus 15 so that electrodes in the lead are near the placement site and can make contact with the requisite pain nerve fibres in the disc 20. Lead 10 typically contains more than one electrode 5, and often can have 8, 16 or more electrodes, which provide the direct stimulation of the nerves in the disc area during system operation.

During implantation, the introducer 30 is passed closely adjacent to the facet joint 40 of the spinal column 50 and into the outer portion 15 of the disc or the annulus. Introducer 30 can be shielded or unshielded. Shielding may be used for impedance monitoring during insertion, which assists in determine the insertion depth into the annulus.

Once the lead is properly placed at the placement site, introducer 30 is then removed. A connector 55 connects lead 10 to a power source or generator 60, which may be either external or implanted. Introducer 30 has a curved tip 70 to facilitate placement of the lead to the placement site. The lead with stimulating electrodes can be placed both across the posterior portion of the disc or alternatively around the periphery in any configuration to allow juxtaposition of the electrodes at the placement site to the requisite nerve fibres.

Figure 2:
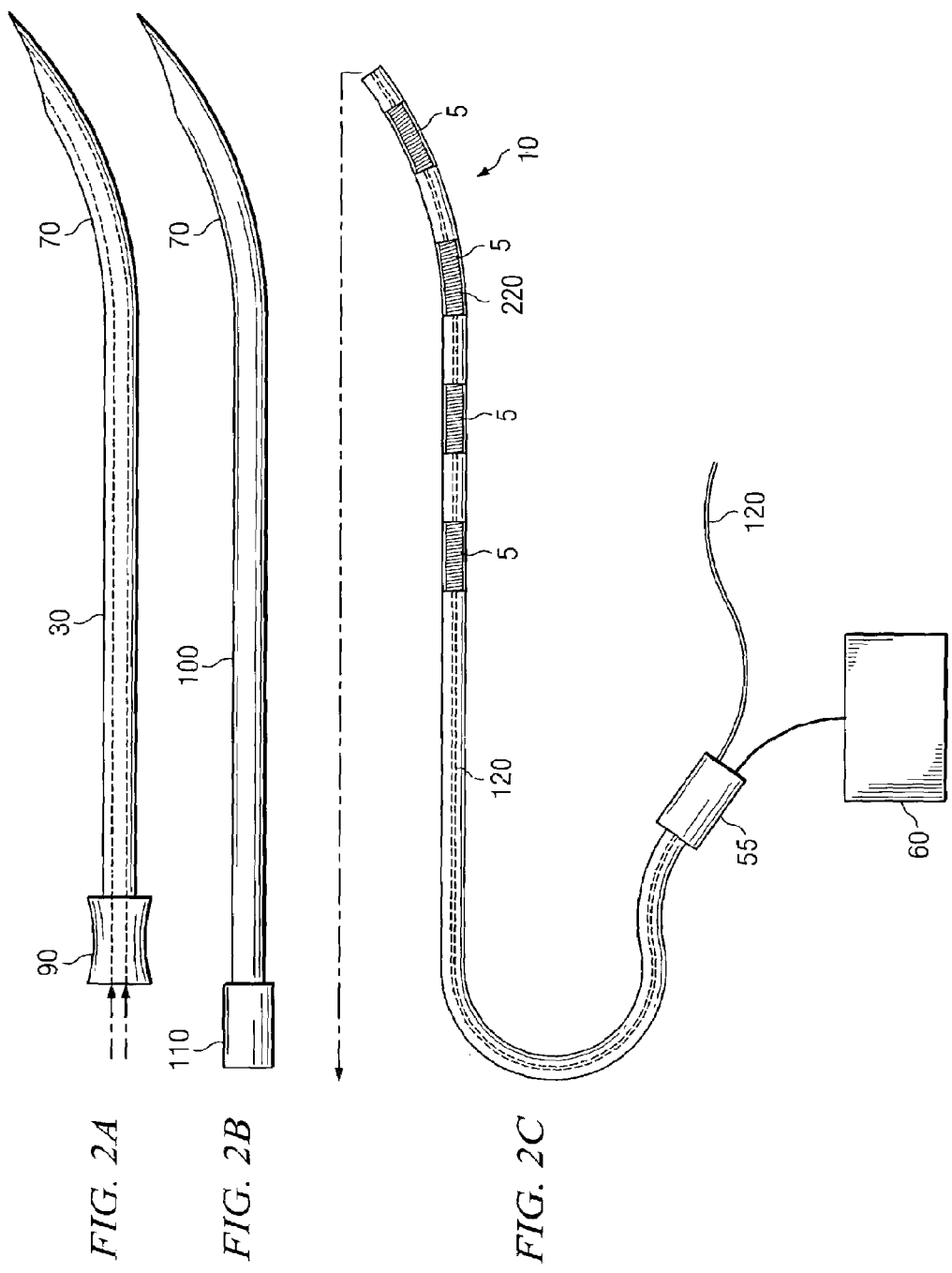
FIGS. 2A, 2B, and 2C shows a system of curved tip introducer and a lead in accordance with the one embodiment of the present invention.

In FIG. 2C, one embodiment of the components of a trial lead are illustrated. Those skilled in the art will recognize that the lead described in each of the figures, including FIGS. 2A-2C, can be either a trial lead or a permanent lead. Lead 10 with its flexible shaft 220 and connector 55 is connected to an impedance monitor and stimulation/power generator 60. Lead 10 contains one or more electrodes 5 thereon, which provide the direct stimulation to the placement site during operation. This stimulating lead is passed down an introducer 30 with a curved tip 70 and a hub 90 to facilitate steering as shown in FIG. 2A. This is performed after the stylette 100 as shown in FIG. 2B of the introducer 30 is removed. The stylette 100 also has a connecting hub 110.

Figure 3:
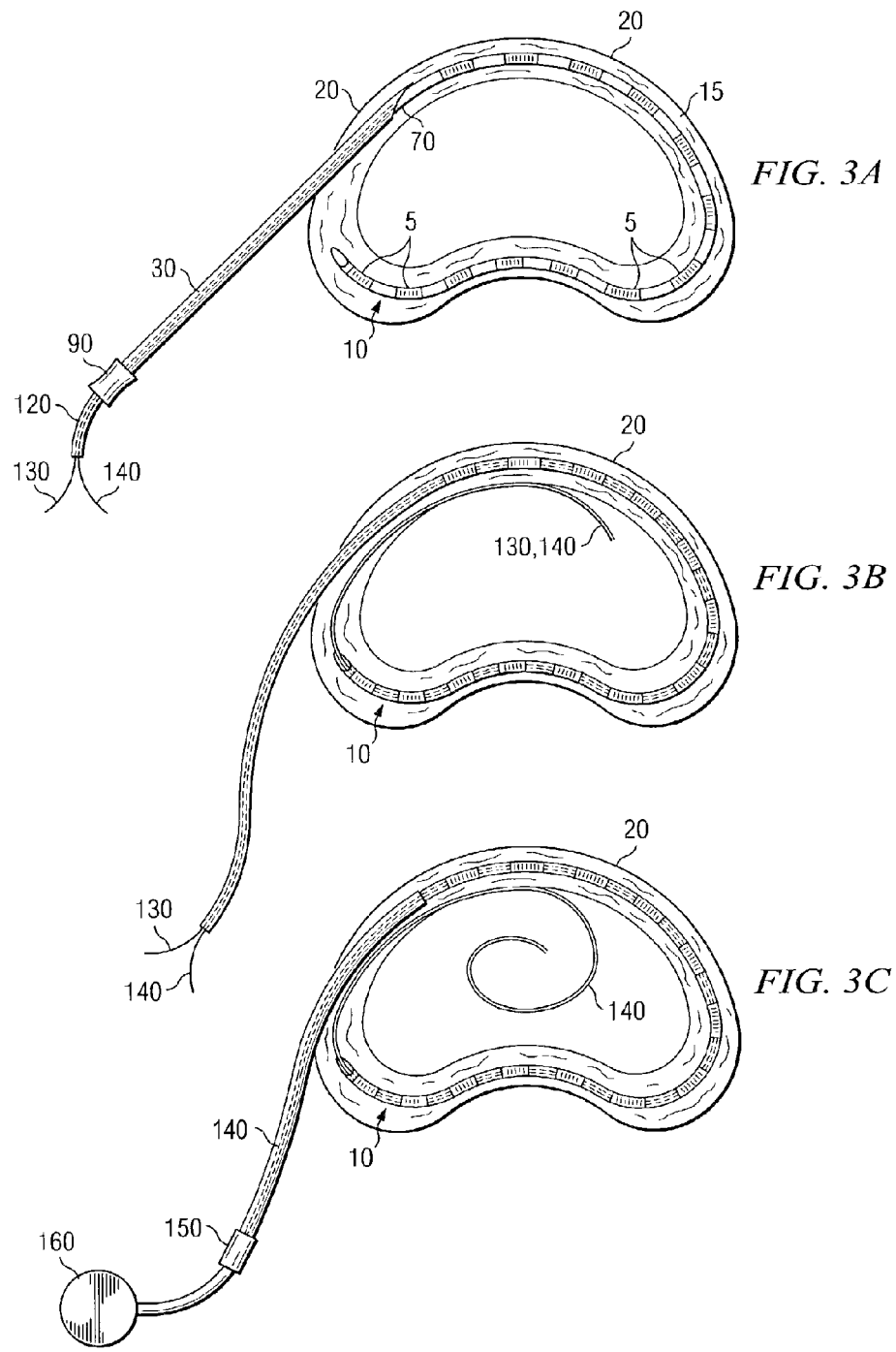
FIGS. 3A, 3B, and 3C show different embodiment configurations of a permanent lead inside with or adjacent to the intervertebral disc.

FIGS. 3A-3C illustrate the possible placement, for certain embodiments, of a permanent implanted lead at the placement or stimulating site. It is envisaged that the introducer 30 is to be passed into the disc 20 in a more lateral position to avoid any conflict with the nerve root.

In FIGS. 3A-3C, the introducer 30 is aimed to pass into or adjacent to the anterior portion of the disc 20 so that the lead 10 curves around the annulus 15 from the anterior portion to the posterior portion of the disc. Lead 10, as shown in FIG. 3A, contains at least one or more electrodes 5 therein, which provide the direct stimulation during operation of the lead, once connected to generator 60. This will achieve the same juxtaposition of lead 10 and pain nerve fibres in disc 20 at the trial stimulating lead placement site as described previously in FIG. 1. Introducer 30 for the permanent lead 10 also has a curved tip 70 and a hub 90 for steering. It is envisaged that the lead will have a central stiffening stylette 120 which will be removed in the case of the trial lead but may be partly retained in the implanted lead 10.

The central stylette 130 will have a modification in the permanent lead 10 such that after the stylette 130 is advanced further into or around the disc 20 than lead 10 itself, then a portion of the central stylette 130 will be removed allowing the retained portion 140 to curl in upon itself and act as a locking or anchoring device for the permanent lead at the placement site in the disc. This prevents displacement and migration of the lead 10 away from the placement site. It is envisaged that lead 10 can be removed in the future if the portion of the central stylette 130 that is removed is replaced, thus straightening the retained portion of stylette 140.

In one embodiment of the present invention, the retained portion of stylette 140 can have a metallic memory such that it can adopt a predetermined shape to anchor the lead and prevent lead migration. It is envisaged that the retained portion of stylette 140 will act as an anchor by adapting to a pre-stressed shape. Alternatively, other forms of anchoring the electrode could be utilized such as an inflatable balloon or surgical fixation.

Lead 10 is connected via an implanted connector 150 to a stimulator or generator 160. Generator 160 may be an implantable device with an internal power source, or alternatively, a radiofrequency receiving coil which is also fully implanted. Such a receiving coil receives power transmitted through the skin.

In a further embodiment, a permanent lead could be physically separated from the power generator by a transmitting and receiving coil. This will prevent the need for direct connecting leads that exit the disc.

Figure 4:
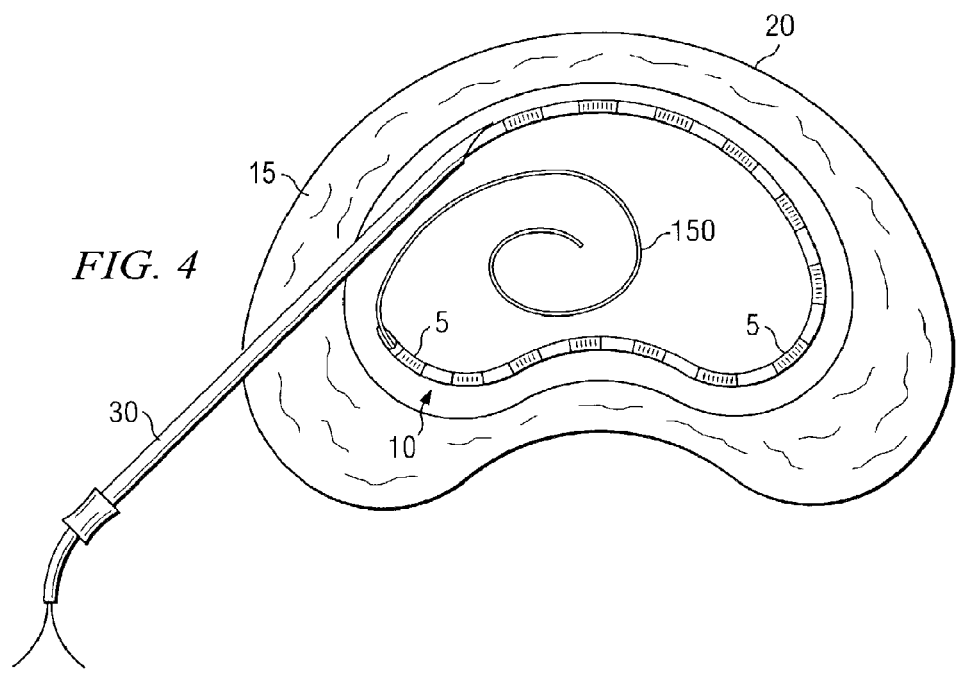
FIG. 4 shows a system of curved tip introducer and a lead in the nucleus in accordance with one embodiment of the present invention.

FIG. 4 shows one embodiment of the present invention during implantation of the lead in the nucleus. As mentioned, it is believed that nerve endings that are involved in disc pain can appear at or in the nucleus. In FIG. 4, the introducer 30 inserts the lead 10 through the annulus 15, and into the nucleus. Once in the nucleus, the lead is placed near the placement site and the anchor 150 is locked into position to anchor the lead in the proper location. One further reason to locate the lead in the nucleus is to ensure that the electrodes are near the proper location, should the pain sensation transmitted via the nerves near the annulus/nucleus interface or in the edge of the annulus near the nucleus interface.

Figure 5:
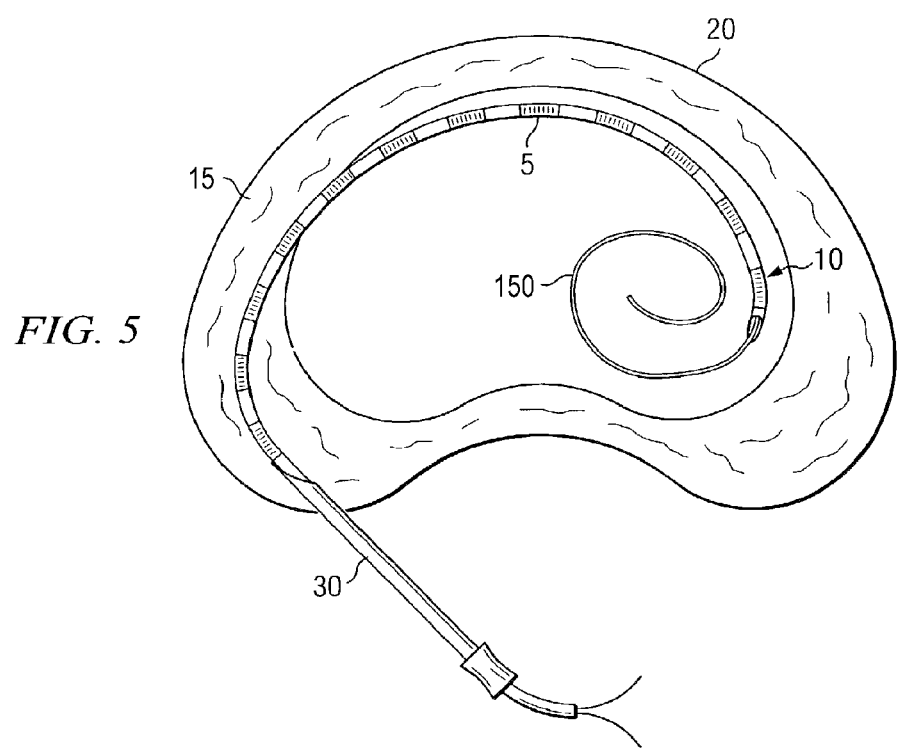
FIG. 5 shows a system of curved tip introducer and a lead in accordance with one embodiment of the present invention.

FIG. 5 shows one embodiment of the present invention during implantation of the lead in the nucleus. In FIG. 5, the introducer 30 inserts the lead 10 partially through the annulus 15 so that the lead is place in between the annulus and the nucleus. Once at the placement site in between the annulus and the nucleus, the lead is anchored by anchor 150 and locked into position to anchor the lead in the proper location. One further reason to locate the lead in the nucleus or at the nucleus/annulus interface is to ensure that the electrodes are near the proper location, should the pain be caused from nerves near the annulus/nucleus interface or in the edge of the annulus near the nucleus interface.

FIGS. 8A and 8B show another embodiment of the present invention during implantation of the lead at the placement site adjacent to the disc. Because of the proximal location of the nerve endings to the placement site exterior to the disc, placement of the lead at this location will allow the nerve endings to benefit from the stimulation effect, without having to enter into the disc. This has safety implications, by reducing the chance of disc space infections, because the leads are not interior to the disc.

In FIG. 8A, either one or two leads 10 are placed around the outside of the disc annulus 15 at the desired placement site or affected area. FIG. 8A shows a percutaneous approach from the patient's posterior side. FIG. 8B shows an endoscopic approach (from the anterior side). It is important to note that either one or both leads may be applied to either side of the affected disc, depending on the location for the desired stimulation or placement site.

Figure 9A:
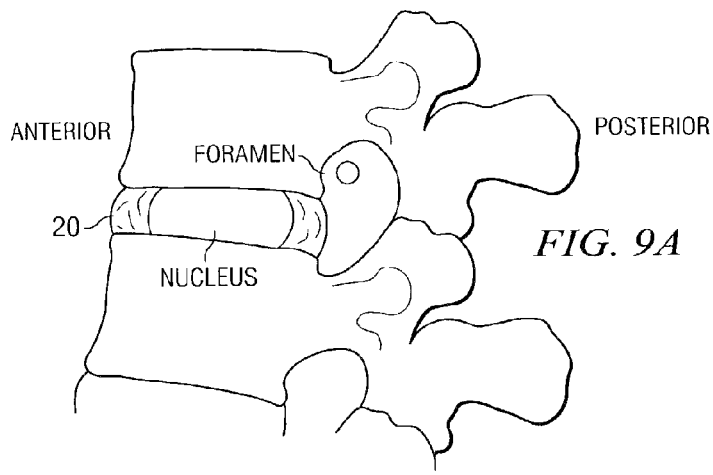
FIG. 9A shows a lateral view of a healthy disc and FIG. 9B shows a lateral view of a narrow degenerate disc.
Figure 9B:
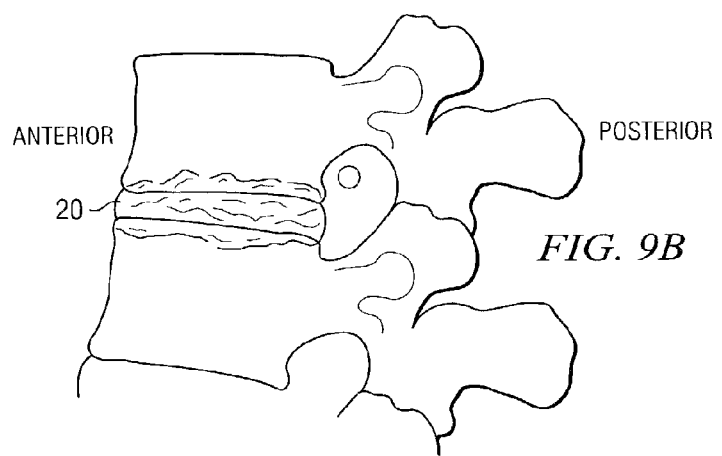
Figure 10:
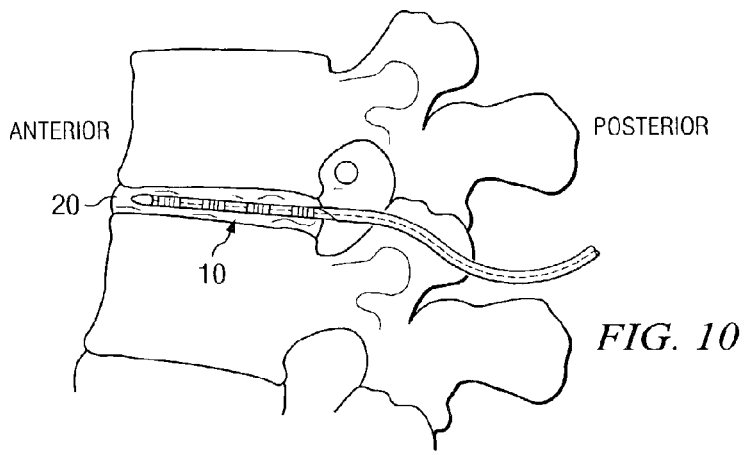
FIG. 10 shows a lateral view of a degenerate disc with one embodiment of the present invention.

FIGS. 9A, 9B and 10 show a lateral view of an affected disc and a lead placement on the outside of such a disc. In FIG. 9A, a healthy disc is shown with a healthy disc annulus 15. FIG. 9B shows a narrowing of a degenerated disc 20. Fissures have narrowed the disc and there is no clear delineation between the disc annulus and the nucleus. Additionally, end plate (modic) changes have occurred. FIG. 10, shows a lateral view of lead 10 located at the placement site in the narrowed degenerated disc. FIG. 10 could represent either lead 10 located within the disc annulus or nucleus, as described herein, or lead 10 can be located outside the disc annulus as shown in FIG. 8A or 8B (FIG. 10 showing a posterior placement in this case).

Figure 6:
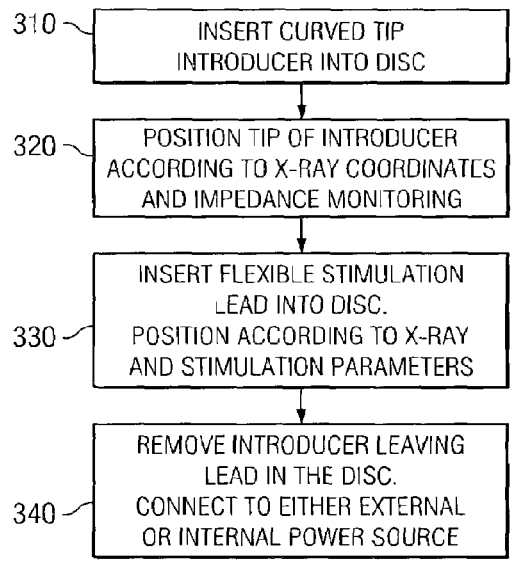
FIG. 6 shows a flow chart of the operation in accordance with the present invention.

FIG. 6 illustrates the methodology of the present invention. In step 310, the doctor inserts the introducer into or just adjacent to a disc. As mentioned above, the introducer has a curved tip to assist in the introduction of the lead. Next, in step 320 the doctor positions the tip of the introducer in or adjacent to the disc according to X-ray coordinates and impedance monitoring. In step 330, the doctor inserts the flexible stimulation lead into or alongside the disc. Positioning the lead at the placement site is accomplished using the X-ray coordinates and the stimulation parameters. The stimulation parameters are determined during the trial insertion procedure to provide the optimal stimulation settings. Finally, in step 340, the introducer is removed and the lead remains in or adjacent to the disc. The lead is then connected to the external or internal power source. The power source will have the stimulation parameters loaded into its memory. Once connected, stimulation of the disc can begin.

As such, an apparatus and method for making such apparatus is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

The invention claimed is:

1. A method of treating chronic discogenic pain in a patient, the method comprising:
    advancing an introducer into the patient from a site proximate to a facet joint of the patient to a site that is directly adjacent to a disc of the patient;
    advancing a stimulation lead with a plurality of electrodes through the introducer device;
    steering the stimulation lead, using a stiffening stylet, while advancing the stimulation lead out of the introducer device to follow a path within the patient that generally follows a path directly about or within the disc of the patient;
    coupling the stimulation lead to an implantable pulse generator;
    testing a plurality of stimulation parameters to identify a stimulation pattern for the patient optimal to treat chronic discogenic pain of the patient; and
    operating the implantable pulse generator, according to the optimal stimulation pattern, over at least multiple days to generate electrical pulses for delivery to tissue of the patient to treat said chronic discogenic pain of the patient.

2. The method of claim 1 further comprising:
    deploying an anchoring mechanism through the stimulation lead to hold the stimulation lead at a target location within the patient.

3. The method of claim 2 wherein the anchoring mechanism is deployed within the disc of the patient.

4. The method of claim 3 wherein the anchoring mechanism comprises a shape memory wire that is adapted to coil within the disc of the patient.

5. The method of claim 2 wherein the anchoring mechanism comprises a balloon structure.

6. The method of claim 5 further comprising inflating the balloon structure to secure the stimulation lead.

7. The method of claim 2 wherein at least some of the electrodes of the stimulation lead are disposed outside the confines of the disc to recruit fibers of an annulus fibrosis that are recruited by the electrical pulses.

* * * * *